US005434341A

United States Patent [19]

Outzen

[11] Patent Number: 5,434,341

[45] Date of Patent: Jul. 18, 1995

[54] XENOGENEIC LYMPH NODE IN MAMMARY FAT PAD

[75] Inventor: Henry C. Outzen, Redwood City, Calif.

[73] Assignee: Systemix, Inc., Palo Alto, Calif.

[21] Appl. No.: 927,240

[22] Filed: Aug. 7, 1992

Related U.S. Application Data

[63] Continuation of Ser. No. 394,939, Aug. 17, 1989, abandoned.

[51] Int. Cl.[6] .............................................. A61K 35/00

[52] U.S. Cl. ....................................... 800/2; 424/578; 424/580; 424/582; 424/553; 424/93.7; 800/DIG. 5

[58] Field of Search ............. 800/2, DIG. 5; 424/578, 424/580, 582, 553, 93.7

[56] References Cited

PUBLICATIONS

Bosma et al., Nature 301: 527–530 (1983).
McCune et al., Science 241: 1632–1639 (1988).
Dubois et al., Differentiation 35: 72–82 (1987).
Sheffield et al., J. Dairy Sci. 69: 1141–1147 (1986).

*Primary Examiner*—Jasemine C. Chambers
*Attorney, Agent, or Firm*—Bertram I. Rowland; Pamela J. Sherwood

[57] ABSTRACT

Methods and chimeric immunocompromised hosts comprising functional xenogeneic organs are provided, particularly hematopoietic organs, where the xenogeneic organ is engrafted into a mammary fat pad. Exemplary is the engrafting of lymph node with mesenteric tissue comprising small portions of blood vessels transplanted into mammary fat pad of a scid/scid mouse. The engraftment in the mammary fat pad provides for efficiencies in transplantation, higher success rate of transplantation, and improved growth of the transplanted organ.

6 Claims, No Drawings

XENOGENEIC LYMPH NODE IN MAMMARY FAT PAD

This is a continuation of application Ser. No. 07/394,939 filed Aug. 17, 1989, now abandoned.

TECHNICAL FIELD

The field of this invention is the transplantation of lymph nodes in heterologous immunocompromised mammalian hosts.

Background

The use of heterologous transplants in a host has found wide application in research and therapy. The ability to transplant tissue from one host to another allows for opportunities of scientific investigation which are not available in the source host. Of particular interest has been the transfer of xenogeneic neoplastic tissue into an immunocompromised host for study of the neoplastic tissue, its response to drugs and changes in the environment of the tissue. There is also interest in being able to grow normal tissue in a foreign host, where the foreign tissue is capable of growing and functioning. In this way, various aspects of the foreign tissue may be studied in an environment simulating its natural environment.

Recently, there was reported the transplantation of normal human fetal tissue into a scid/scid mouse (McCune et al., *Science* (1988) 241:1632–9). The authors describe the introduction of human thymus and lymph node fetal tissue into the kidney capsule of a scid/scid mouse. The fetal tissue was found to grow and function, and the thymus assume a substantially natural architecture, where the organs were capable of interacting.

The kidney capsule as a site for introduction of xenogeneic tissue has many deficiencies. It is physically difficult to introduce the tissue, so that there is a significant number of failures in producing functional organs. Also, vascularization is not as extensive as one would wish. In addition, the lymph node did not maintain a desirable growth pattern. There is, therefore, interest in being able to develop alternative sites and methods for introduction of xenogeneic tissue into anatomical sites of target hosts.

Relevant Literature

Outzen and Custer, *J. Natl. Cancer Inst.* (1975) 55:1461–1466 describe the growth of human normal and neoplastic mammary tissue in a cleared mammary fat pad of a nude mouse. Sheffield and Welsch, *Int. J. Cancer* (1988) 41:13–19 report transplantation of human breast epithelia to mammary-gland-free fat-pads of athymic nude mice. Dubois et al., *Differentiation* (1987) 35:72–82 describe human breast epithelial xenografts, where human epithelium is grafted onto mammary and non-mammary sites. (See also EPA 88.312222.8, filed Dec. 22, 1988.)

SUMMARY OF THE INVENTION

Methods and hosts are provided comprising xenogeneic functioning lymph nodes growing in a mammary fat pad of an immunocompromised host. Desirably, the mammary fat pad is cleared of the mammary gland. The method involves exposing the mammary fat pad and inserting the xenogeneic fetal lymph node tissue with surrounding mesenteric tissue into the mammary fat pad and closing the incision. The lymph node tissue is found to be rapidly vascularized and rapidly grows to a lymph node having substantially conventional architecture.

DESCRIPTION OF SPECIFIC EMBODIMENTS

Chimetic hosts are provided comprising a functioning xenogeneic lymph node vascularized in a mammary fat pad of an immunocompromised host. The chimetic host is obtained by introduction of a fetal lymph node in conjuction with the mesenteric tissue. The fetal tissue is highly vascularized, grows rapidly, and assumes a substantially normal architecture associated with the lymph node source host.

The chimeric host is obtained by isolating tissue from a lymph node from a fetus of a source host, where the lymph node tissue further comprises surrounding mesentery tissue. The immunocompromised host is prepared for the lymph node by making an incision in the host so as to expose the mammary fat pad. If desired, the mammary fat pad may be cleared of the mammary gland in accordance with conventional techniques. After making the incision, the mammary fat pad may be modified, by removal of a small portion of the fat pad, using sharp forceps, a trocar, or other means for creating a space for introduction of the lymph node tissue. The space formed should readily accommodate the lymph node tissue and allow the lymph node and mesenteric tissue to be comfortably placed in the space and retained. Once the lymph node tissue has been introduced, the incision may be closed and the host grown. The growth of the lymph node may then be monitored by reopening the incision and visual inspection or by other non-invasive technique, as appropriate.

For a mouse host, conveniently, the inguinal mammary fat pad, the fourth mammary fat pad, may be employed, since it is conveniently located and of convenient size. An incision is made through the skin in the under portion of the mouse between the rear legs, so that the two inguinal mammary fat pads may be exposed. The mammary fat pad is located at the intersection of three arteries. A mouse lymph node is located directly beneath this intersection. The transplant is desirably placed medially to this intersection. After exposing the mouse fat pad, using forceps, a hole is punched into the mammary fat pad using sharp forceps or a trocar.. The lymph node and mesenteric tissue is then placed into the hole. The incision then is closed and the mouse maintained on a normal diet.

The subject invention is concerned with only those non-human hosts which have mammary fat pads. This includes a wide variety of mammals. The mammals are immunocompromised in normally inheriting the desired immune incapacity or where the immune incapacity may be created. For example, hosts with severe combined immunodeficiency, known as scid/scid hosts, are available. Rodentia, particularly mice, and equine, particularly horses, are presently available as scid/scid hosts (hereafter referred to as SCID hosts). The SCID hosts lack functioning lymphocyte types, particularly B-cells and some T-cell types. In the SCID mouse, the genetic defect appears to be a non-functioning recombinase, for the germline DNA is not rearranged to produce functioning surface immunoglobulin and T-cell receptors.

The immunocompromised hosts may also be a result of a non-functioning thymus, e.g., nude mice, irradiation, so as to destroy stem cells, treatment with stem cell specific cytotoxic agents, cytotoxic agents specific for rapidly dividing cells, e.g., anti-asialogycoprotein GM-1, or the like. At a minimum, usually an immunocompromised xenogeneic host will lack functioning B- and at least some types of T-cells, particularly as a genetic defect in B- and/or T-cell germline rearrangements. Therefore, in many instances the immunocompromised host may have functioning organs associated with the immune system such as thymus, spleen, lymph node, pancreas, tonsils, gut (mucosa), etc.

The immunocompromised host may be further modified by breeding between an immunocompromised host and a host having another phenotype of interest. For example, the C.B17 scid/scid strain might be backcrossed with suitable murine strains having low or no NK activity. In this way, a mouse strain lacking T-, B-, and NK cells might be produced. Such a host would predictably better accept and maintain xenogeneic tissue and cells.

For the most part, the lymph node tissue transplant will be only one of other tissues which may be transplanted into the host. The lymph node may serve in the development of a hematopoietic system in the immunocompromised host for variety of purposes. For example, in addition to the lymph node tissue, other hematopoietic components may be included, such as stem cells, embryonic yoke sac, fetal liver, thymus, spleen, fetal or adult bone marrow tissue, pancreatic tissue, appendix tissue, tonsil tissue, and the like. These tissues may be also introduced into the same or different mammary fat pad as the lymph node or may be placed at other sites. Sites for introduction may include under the spleen capsule, abdominal wall, muscle, under the renal capsule, the peritoneum, the peritoneal lining, brain, subcutaneous, vascular system, spleen, spinal cord, blood, liver, membranous sacs or capsules of various tissue, the retroperitoneal space, skin, reproductive organs, etc.

Desirably, progenitor tissue will be introduced which will grow into a functioning organ. Introduction of the tissue may be achieved by injection, implantation, or joining blood vessels (and other vessels if necessary) of the donor and host, using intravenous catheters, trocars and/or surgical incision, or the like. The tissue or cells of interest will generally be normal tissue or cells (as distinguished from neoplastic or defective tissue or cells).

The organs which are transplanted into the mammary fat pad desirably have small portions of the blood vessels feeding into the particular organ. With the lymph node, mesenteric tissue is included, which comprises portions of efferent, afferent and lymph vessels generally of not more than about 2 mm extent, frequently of not more than about 1 mm extent. The vessels are found to rapidly anastamose, forming functional junctions with the host vascular system. Thus, vascularization is rapidly achieved with efficient bonding between the xenogeneic blood vessels.

With various organs, one may include with the tissue from the organ, surrounding connective tissue, fascia, etc.

Any mammalian host may be employed other than the presently available mice and horses (equine), which hosts may include members of the ovine, bovine, capfine, lagomorpha, primate (other than human), porcine, canine, feline, etc., or other warm-blooded vertebrates, such as birds. Of particular interest are laboratory animals, such as mice, rats, guinea pigs, e.g., capybara, and rabbits, as well as domestic animals, such as primates other than humans, cows, sheep, pigs, or the like. The xenogeneic host will usually be of a different species or family from the host source of cells.

The xenogeneic host will be an immunocompromised mammal, other than human, where, for the most part, the donor cells will be human cells, although cells from sources other than members of the same family of the xenogeneic host may also find use. The xenogeneic hosts may have defects at various levels resulting in an immunocompromised host. The defect may result in loss of functional antibody expressing or independent lymphocytes, such as natural killer (NK) cells, lymphokine activated killer (LAK) cells, antibody dependent cytotoxic (ADCC) cells, tumor infiltrating lymphocytes (TIL), macrophages, etc.

The recipient mammalian host may be subject to a variety of immune defects. Of particular interest is the defect resulting in non-functional T- and B-cells. Such dysfunction may be achieved with SCID (severe combined immunodeficiency) animals. In the future, e.g., using transgenic cell-depletion techniques, scid animals of other species may be developed. Other malfunctions may include nonfunctional stem cells, lack of surface membrane proteins associated with T-cell and B-cell function, incompetent receptors, e.g., T-cell receptor and surface immunoglobulin receptor, deficiency in T-cell and B-cell maturation, deficiency in natural killer cell activity, deficiency in one or more interleukins and/or other growth factors, and non-functional thymic, lymph node, splenic or bone marrow stroma.

Besides the phenotypic deficiency, further reduction in immunocompetence may be achieved by irradiation of the host biological immunosuppressives (e.g., cyclophosphamide, cyclosporine, etc.), or use of immunocytotoxic labels as indicated previously, e.g., antibodies specific for cells of the lymphoid (including natural killer cells or myelomonocytic) lineages. Particularly where immunocompetence may be provided by the tissue introduced into the host, native immunocompetence can be enhanced above the low level naturally present in the particular phenotype of the host.

In appropriate situations, one or more organs may be removed for particular purposes. For example, a splenectomy may be performed to provide longer-term reconstitution of circulating red and other hematopoietic cells. Other organs may be removed for introduction and study of a xenogeneic organ. Bone marrow may be removed or destroyed by selective irradiation for introduction of xenogeneic bone marrow. Host stromal cells may be removed to provide xenogeneic stromal cells for a more natural environment for xenogeneic stem cells.

The host will usually be of an age less than about 25% of the normal lifetime of an immunocompetent host, usually about 1 to 20% of the normal lifetime. Generally, the host will be at least about 3 weeks old and large enough to manipulate for introduction of the mammalian cells at the desired site. For example, mice which may be considered to have about a 2–4 year lifetime are used at about 3 to 10, usually 4 to 8 weeks, of age. Growth of the donor tissue within the host will vary with the organ, usually being at least 5-fold, more usually at least a 10-fold and may be a 100-fold or more increase in size (volume), being retained for at least 20 days, usually at least 40 days at the enhanced size.

In addition to the hematopoietic cells and organs, other tissue or cells may be employed in the same host. These cells generally will be normal tissue or cells and may be associated with the central nervous system, the autonomic nervous system, brain, liver, bone, digestive system, reproductive system, bladder, gallbladder, joints, pancreas, retina, nerve, spleen, adrenal gland, etc. Other organs which may be employed include tissue from the brain, such as cerebrum, cerebellum, medulla oblongata, cortex, pons, corpus callosum, cerebral peduncle, hippocampus, thalamus, basal ganglia, etc., as well as portions thereof. Other tissue may include placental tissue, synovial tissue, vascular tissue, esophageal tissue, membrane tissue, smooth muscle tissue, muscle tissue, bone tissue, cardiac tissue, cartilage, mucosal membranes, etc.

In some instances, defective tissue or cells may be grown to investigate the genetic disease, expand the source of defective DNA, investigate the effect of drugs and treatment regimens, and the like. Tissue of interest may include $\beta$-thalassemic cells, cells associated with Huntington's disease or Duchenne's syndrome, cells with fetal anomalies including trisomy 21, cells from diabetic pancreas, cells from patients with Alzheimer's disease or myasthenia gravis, and other disorders of the central nervous system, etc.

The source of the tissue may vary from embryo yolk sac to fetal tissue, having a gestational age of at least about 4 weeks, more usually at least about 6 weeks, ranging up to adult tissue, depending upon the nature of the tissue or organ. Preferably, the tissue will be from a child of less than about 3 years, preferably less than about 1 year and at or younger than neonate, more preferably being fetal tissue of from about 7 to 24 weeks.

For different organs differently aged tissue may be preferred. For fetal tissue, human lymph node is desirably equal to or greater than about 15 gestational weeks (g.w.), preferably 16–20 g.w.; for human thymus, from about 9 to 24 g.w., preferably less than about 20 g.w.; bone marrow tissue, from about 16 to 24 g.w.; and for human fetal liver, from about 10 to 24 g.w., preferably from about 13 to 22 g.w.

The tissue may be fresh tissue, obtained within about 48 hrs of death, or freshly frozen tissue, tissue frozen within about 12 hrs of death and maintained at below about −10° C., usually at about liquid nitrogen temperature (−70° C.) indefinitely. The tissue may be from an organ implanted in the chimetic host, where the tissue may be removed from 2 to 4 weeks after implantation, or longer. In this manner, the tissue originally obtained from the host source may be greatly expanded, substantially increasing the total number of chimeric hosts which may be obtained. The tissue obtained from the chimeric host may be treated analogously to the tissue obtained from the original tissue source host. The tissue, other than lymph node tissue, may be provided as individual cells freed of attached stromal elements, as a dispersion, or as small tissue slices, generally of from about 0.5 mm to 4 mm, more usually from about 1 mm to 2 mm, generally of a thickness in the range of about 1 to 2 mm, so that the sections can easily fit into a trocar used for implantation, usually conveniently of about 15- to 20-guage. Normally, the cells will not have been subject to culture in vitro for any extended period of time, e.g., three days or greater; for special purposes, however, such pre-implantation culture in vitro may prove desirable. In some cases, particularly lymph nodes, whole or partial organ grafts may be transplanted by anastomosing donor and host blood vessels, lymphatic vessels, and other vessels such as ureters, etc.

As appropriate, dispersed cells may be employed, where the relevant organs are teased apart to yield viable cells in suspension. Desirably, the suspension cells may be enriched for the particular cells of interest. For example, with fetal liver cells, the suspension cells may be enriched for hematopoietic precursors by ficoll-hypaque density gradient centrifugation. Cells may also be enriched by other techniques, such as fluorescence-activated cell sorting, panning, magnetic-bead separation, elutriation within a centrifugal field, or rosetting.

In some instances, it may be desirable to enrich cells by killing or removing other cells. This may be achieved by employing monoclonal antibodies specific for the undesired cells in the presence of complement or linked to a cytotoxic agent, such as a toxin, e.g., ricin, abrin, diptheria toxin, or a radiolabel, e.g., $^{131}I$ or the like Immunoaffinity columns may be employed, which allow for specific separation of either the desired or undesired cells, depending upon the nature of the mixture.

Depending upon the tissue which is introduced into the host, the nature of the host, and the combinations of tissue employed, various results can be achieved. Of particular interest in the hematopoietic system is the production of sets and subsets of cells, particularly T-cells and/or B-cells. For example, by using fetal liver stem cells in conjunction with a thymus and lymph node from the same species or host (allogeneic or syngeneic) in the immunocompromised host, T-cells, B-cells, and myelomonocytic cells can be produced which are native to the source host. The production of the T-cells, as well as any other source host cells, may be enhanced by introducing various lymphokines, cytokines, and growth factors from the tissue host source into the mammalian host. In this way, the growth of the desired cells may be further enhanced. Illustrative factors include each of interleukins 1–7, particularly IL-1, -2, and -3; M-, G-, and GM-colony stimulating factor, interferons-$\alpha$, -$\beta$, and -97 , monokines, growth factors, etc. The amount that may be added will vary depending upon the nature of the mammalian host, the nature of the cell, as well as the nature of the factor.

In order to enhance particular subsets of T-and/or B-cells, the mammalian host may be immunized with an antigen of interest to expand the population of T-cells and B-cells which bind to the particular antigen. The mammalian host may be subjected to extra immunizations to enhance further the desired population. In this manner, B-cells may be produced which are specific for the antigen and may be used as splenocytes, lymph node lymphocytes, or other peripheral blood lymphocytes for fusion with an appropriate fusion partner to produce hybridomas in conventional manners or be immortalized with EBV. Various myeloma cells exist for fusion with primate cells, particularly human cells, such as reported in U.S. Pat. Nos. 4,574,116; 4,594,325; and 4,451,570. Alternatively, T-cells may be immortalized to provide for T-cells carrying T-cell receptors which may be used for stimulating B-cells, mixed lymphocyte reactions, evaluating immunodominant sequences, affinity columns for B-cells, particularly in association with an immunodominant sequence, or for cytotoxicity or inflammatory reactions against relevant (e.g., neoplastic) target cells. In addition, various colonies of monocytes, granulocytes, macrophages, eosinophils, neutrophils, myeloid cells, blast cells, precursor cells, and the like may be produced and isolated.

Also, the presence of the foreign (source host) tissue in an immunocompromised host may be used to study the effect of various compounds on the growth, viability, differentiation, maturation, transformation, or the like, of the foreign cells in a live host. Thus, the immunocompromised host may be used to study the effect of variation of a condition on a symptom or indication of a disease. By "condition" is intended a physical chemical or biological property; e.g., temperature, electric potential, ionic strength, drugs, transformation, etc.

Normally, the tissue is vascularized. Thus, various drugs may be administered to the host and the effect on a particular tissue determined by noninvasive or invasive techniques. Non-invasive techniques include NMR, CAT scans, fluoroscopy, roentgenography, radionuclide scanning, ultrasonography, electrocardiography, electroencephalography, evoked potentials, etc. Invasive techniques include biopsy, autopsy, laparotomy, laparoscopy, intermittent intravenous blood sampling, or intravenous catheterization, etc. Convenient placement of various devices, e.g., catheters, electrodes, etc., may be performed for continuous monitoring. Thus, the host may be used to determine the carcinogenicity of various compounds to different foreign tissues, the effect on growth and viability of various foreign tissues, the effect of combinations of compounds, e.g., drugs, or the like. In addition, by providing for pathogenic infection of the foreign tissue, the effect of various drugs in protecting the host tissue from the pathogen, as well as being cytotoxic to or suppressive of the pathogen in a cellular environment can be determined.

The chimetic host may also be used for evaluating the cytotoxicity of various drugs toward the foreign tissue, for example, for screening for investigative new drug applications. In addition, the chimetic host may be used to evaluate the drugs as to their efficacy, safety and bio-availability.

Organs may be grown for transplantation, so that tissue from the donor host, particularly syngeneic tissue or allogeneic tissue, may be grown to an organ in the mammalian host and then transplanted to a recipient which is of a species able to accept the organ grown in the mammalian host. The cells may be subject to various manipulations, e.g., transfection, to introduce a new phenotype, correct a defective phenotype, etc.

The mammalian host will be grown in conventional ways. Depending upon the degree of immunocompromised status of the mammalian host, the mammalian host may be protected to varying degrees from infection. Thus, in some instances, a sterile environment or prophylactic antibiosis may be indicated. Prophylactic antibiosis may be achieved for SCID mice with 25–75 mg trimethoprim and 100–300 mg sulfamethoxazole in 5 ml of suspension or in 5 gm food pellets, given 3 days each week. Alternatively, it may be satisfactory to isolate the potential xenogeneic hosts from other animals in germ-free environments after caesarean derivation. The feeding and maintenance of the chimetic host will for the most part follow conventional techniques.

The foreign cells will usually be present for at least two weeks, usually at least four weeks and may be continuously present over periods of three months or more. For the most part, normal cells, tissue, and/or organs may be stably maintained and function for at least 3–6 months, frequently, at least 10 months.

The foreign cells are capable of remaining viable in the immunocompetent host and will be capable of functioning in the source host and frequently capable of functioning in the xenogeneic host. That is, besides carrying on normal metabolic processes, the cells will respond to ligands, transduce signals, secrete appropriate products and carry on normal functions as carried on by syngeneic or congeneic cells in their wild-type host. Furthermore, where organs are involved, the cells will define a tissue mass with appropriate architecture for the organ function.

The immunocompromised host may be used in a variety of ways associated with its ability to provide an environment in which stem cells may proliferate and differentiate. Thus, the host may be employed to detect the presence of stem cells in a cellular composition, which may be homogeneous or heterogeneous. A cellular composition, such as bone marrow, may be separated into fractions using, for example, a fluorescence activated cell sorter ("FACS"). The fractions may then be injected intravascularly into the host. After sufficient time for the cells to differentiate, tissue or blood may be removed from the host to serve as a source of peripheral blood lymphocytes or other hematopoietic cell, e.g., erythroid, myeloid and platelets. If necessary, the stem cells could be MHC typed to ensure that the mature cells originate from the stem cells, with the stem cells having different MHC antigens from other hematopóietic cells which may be present in the host. The presence of mature cells of the various hematopoietic lineages would be indicative of precursor cells, while the presence of all lineages would be indicative of stem cells. Again, the FACS could be used with advantage to determine the cellular population.

The following examples are offered by way of illustration and not by way of limitation.

EXPERIMENTAL

Methods

1. Mice.

C.B17 scid/scid mice were obtained from Dr. Leonard D. Shultz of The Jackson Laboratory, Bar Harbor, ME. The mice are housed in standard isolator cages within a routine animal holding facility. Under these conditions, they have a lifespan that is considerably shorter than that of other inbred immunocompetent strains (e.g., 1–2 yrs vs. 3–4 yrs). The cause of death is normally related to opportunistic infection (most often by Pneumocystis carinii). Protocols to prevent such infections by caging in microisolators (Lab Products, Inc.) and by administering prophylactic antibiotics (trimethoprim/sulfamethoxasole) to the mice are being employed (see above) using as guidelines protocols developed for the prophylaxis of patients with AIDS or ARC. In all other respects (e.g., bedding, food, daily light cycles, etc.), the mice are handled as per routine animal holding facility protocols.

2. Collection and preparation of human fetal tissues.

The information that is known about the patient includes the approximate (or where known, the actual) gestational age of the fetus and the given reason for the abortion; in the latter case, also known are the details of any genetic or morphologic anomaly discovered by amniotic fluid analysis and/or ultrasonography (e.g., chromosomal defects, anencephaly, hydrops, etc.). In initial experiments, tissue from fetuses that are apparently normal were used; in later experiments, specifically constructed situations were created in which tissues from fetuses with genetic anomalies were tested.

The tissues are obtained directly in the operating room as fetal parts after elective or medically-induced abortion (with gestational ages ranging from 7-24 weeks). Without maintaining strict sterility, these parts are taken immediately to a tross dissection room. The desired tissues are identified, dissected out, placed into RPMI 1640 medium with 10% fetal calf serum, and transported directly to another lab. In those situations in which "whole organ" transplants (i.e., tissue inclusive of both the stromal elements and of the hematopoietic elements therein) are being performed, the relevant organs are cut into sections that are approximately 1 mm to 4 mm. (A piece of tissue of this size fits easily into the 19-guage trocar that is used for implantation.) In those situations in which dispersed cells are to be injected, the relevant organs are teased apart to yield viable cells in suspension. In the case of fetal liver, the suspension cells are enriched for hemtaopoietic precursors by ficoll-hypaque density gradient centrifugation; the interface layer containing the desired cells is then washed 3x, counted, and brought to approximately $10^8$ cells/mi. For subfractionation of stem cell precursors, fetal liver cells isolated on ficoll-hypaque gradients are subsequently stained with monoclonal antibodies against relevant cell surface markers and isolated by techniques including negative selection with magnetic beads and positive selection on the FACS.

To mark the genetic origin of the donor fetal tissue, HLA historyping is performed on fetal leukocytes or thymocytes using monoclonal antibodies (see below) that recognize common HLA alleles. In this manner, prior to implantation, a histotyped "fingerprint" is obtained by which all subsequent progeny of the introduced stem cells may be specifically followed in the SCID-hu mouse.

Tissue is normally introduced in as fresh a state as possible. Therefore, the tissue collection, preparation, histotyping, and implantation are done all On the same day. Frozen tissue, however, appears to work well in the case of fetal liver cells and fetal thymus tissue. Therefore, aliquots of remaining tissue from each specimen are frozen down at the end of the day in 10% DMSO/50% FCS using standard procedures and then catalogued in a liquid nitrogen storage freezer.

3. Transplantation of lymph node into mammary fat pads.

Recipients are 6-8 weeks of age. All transplantations are performed under sterile conditions in a vertical, sterile, air-flow hood. After receiving transplants, the mice are housed in microisolator cages (Lab Products).

The human mesenteric lymph node with the peritoneal fascia of the mesentery (containing efferent and afferent blood vessels and lymphatics) was obtained as approximately a 2 mm elliptical tissue slice. The prepared SCID mice were removed from the microisolator, in a vertical laminar sterile air-flow hood, anesthetized with pentobarbital sodium (0.01 ml/g body weight; solution of 6.7 mg pentobarbital sodium/ml in 9% ethanol) and taped on sterile operating boards. By an aseptic technique, the number four mammary fat pads were exposed through a midline ventral incision. Sharpened watchmakers forceps were used to create a defect in the mammary fat pad through which the mesenteric lymph nodes were introduced. The ventral skin incision was then closed with 7.5 mm wound clips.

In SCID mice grafted as described above 100% of the mice were found to result in the growth of the lymph node. Anastomoses were found to occur between the blood vessels of the transplant and the host blood vessels. Prompt vascularization was observed, as well as a generation of human primary follicles over a period of 3-6 weeks.

The central artery in the human lymphoid follicule was shown to be of murine origin in a microscopic section. Except for chimetic vascularization and encapsulation by murine fibrous tissue, the architecture of the node was found to be that of a normal human lymph node by immunohistochemistry in histologic sections.

The nodes appeared to grow steadily within the SCID/hu mouse for periods of time ranging from 2-10 weeks.

To further demonstrate the nature of the cells present in the lymph node, the SCID/hu mice which were grafted with the lymph node as described above were inoculated intravenously with an inoculum of HIV. 95% of the SCID/hu mice were found to be viremic 2 weeks after i.v. inoculation with 0.3 ml of HIV-JR-CSF containing approximately 120 ng/ml of HIV p24 antigen. As the dose of input virus was lowered, the time and course of infection was correspondingly delayed. Thus, it was established that the lymph nodes which were grafted in the mammary fat pads were able to function and provide for T4 helper cells which were susceptible to infection by HIV-1 analogous to normal T4 cells in a human host.

It is evident from the above results, that an improved method for engrafting lymph nodes or other normal tissue, particularly of the hematopoietic system, is provided by introducing the organ with its own associated blood vessels feeding into the organ into a host's mammary fat pad. In this manner, the rate of growth of the organ is increased, ease of introduction is achieved as compared to introduction in the kidney capsule, higher efficiencies of engraftment are achieved, so that a more reliable, efficient and economic method for engrafting xenogeneic organs into an immunocompromised host, particularly a small host such as a mouse, is obtained. For lymph nodes, the lymph node tissue has substantial verisimilitude to a normal functioning lymph node.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A C.B17 scid/scid mouse host, comprising viable non-malignant, nontransformed vascularized human fetal lymph node tissue with surrounding mesenteric tissue in a mammary fat pad.

2. A mouse host according to claim 1, wherein said mammary fat pad is cleared of the mammary gland.

3. A mouse host according to claim 1, further comprising at least one of human fetal thymus tissue, human fetal lymphocytes or human fetal liver tissue.

4. A method for producing a chimeric mouse comprising human fetal lymph node tissue engrafted onto a mammary fat pad, said method comprising:

inserting into an exposed mammary fat pad of a C.B17 scid/scid mouse as a result of an incision, human fetal lymph node tissue comprising mesenteric tissue including short portions of afferent, efferent vascular and lymph vessels; and closing said incision and maintaining said mouse whereby said lymph node tissue becomes vascularized and said lymph node tissue grows and functions.

5. A method according to claim 4, wherein said mammary fat pad is the fourth mammary fat pad.

6. A method according to claim 4, further comprising inserting into said mammary fat pad human fetal hematopoietic tissue other than lymph node tissue.

* * * * *